United States Patent
Sones et al.

(10) Patent No.: US 10,393,670 B1
(45) Date of Patent: Aug. 27, 2019

(54) CONTAINER INSPECTION SYSTEM

(71) Applicant: Applied Vision Corporation, Cuyahoga Falls, OH (US)

(72) Inventors: Richard A. Sones, Cleveland Heights, OH (US); Kris Brumbaugh, Marshallville, OH (US); Michael Leo Kress, Uniontown, OH (US); Bryan Murdoch, Stow, OH (US)

(73) Assignee: Applied Vision Corporation, Cuyahoga Falls, OH (US)

( * ) Notice: Subject to any disclaimer, the term of this patent is extended or adjusted under 35 U.S.C. 154(b) by 399 days.

(21) Appl. No.: 15/158,715

(22) Filed: May 19, 2016

(51) Int. Cl.
*G01N 21/90* (2006.01)

(52) U.S. Cl.
CPC ..... *G01N 21/90* (2013.01); *G01N 2201/0637* (2013.01)

(58) Field of Classification Search
CPC .............. G01N 21/90; G01N 2201/0637
See application file for complete search history.

(56) References Cited

U.S. PATENT DOCUMENTS

| | | | |
|---|---|---|---|
| 5,699,152 A * | 12/1997 | Fedor | G01N 21/909 356/240.1 |
| 6,061,125 A | 5/2000 | Thomas et al. | |
| 7,271,889 B2 | 9/2007 | Cemic et al. | |
| 8,004,667 B2 | 8/2011 | Kwirandt | |
| 9,756,239 B2 * | 9/2017 | Okazawa | H04N 5/23222 |
| 2001/0048524 A1 * | 12/2001 | Sones | G01N 21/8806 356/239.4 |
| 2002/0118874 A1 | 8/2002 | Chung et al. | |
| 2006/0126060 A1 * | 6/2006 | Colle | G01N 21/9054 356/239.4 |
| 2007/0237356 A1 | 10/2007 | Dwinell et al. | |
| 2010/0141756 A1 * | 6/2010 | Grote | B65C 9/067 348/127 |
| 2012/0216689 A1 | 8/2012 | Cochran et al. | |
| 2013/0087059 A1 | 4/2013 | Baird et al. | |
| 2015/0336750 A1 | 11/2015 | Coates et al. | |

\* cited by examiner

*Primary Examiner* — Huy T Nguyen
(74) *Attorney, Agent, or Firm* — Medley, Behrens & Lewis, LLC

(57) ABSTRACT

A container inspection system is described herein. The container inspection system includes a light source that emits a flash of light when a container is detected as being in an inspection region. The container inspection system further includes a light director element that receives a portion of the flash of light and forms a tapering field of light that illuminates an exterior surface of a sidewall of the container when the container is in the inspection region. The container inspection system further comprises a camera that generates an image of the exterior surface when such surface is illuminated by the tapering field of light. A computing system receives the image and outputs an indication as to whether or not the container is defective based upon the image.

20 Claims, 12 Drawing Sheets

CONTAINER INSPECTION SYSTEM

BACKGROUND

Production plants for manufacturing containers (such as beverage cans) can produce a very large number of containers, with sophisticated (multicolor) decoration thereon, in a relatively short amount of time. For instance, a conventional decorator in a container production plant can decorate several thousand containers per minute. Container decorations have intrinsic value, as consumers tend to attach perceptions of quality of product based upon the design on the container that holds the product.

Conventionally, there is a lack of robust inspection of exterior surfaces of containers at these container production plants. A known process for container inspection is tasking an operator at the plant to periodically sample containers from a conveyor for visual inspection. For instance, every so often (e.g., every 15 minutes), the operator may be tasked with pulling a small number of containers off of the conveyor and visually inspecting the containers to ensure that the exterior surfaces of the containers are free of readily apparent defects (e.g., to ensure that proper colors are applied to the exterior surfaces of the containers, to ensure that the exterior surfaces of the containers are free of smears, etc.). Using this conventional approach, hundreds of thousands of defective containers may be manufactured prior to the operator noticing a defect on the exterior surface of one or more of the sampled containers. In practice, these (completed) containers must be scrapped, resulting in significant cost to the container manufacturer.

Recently, automated systems have been developed and deployed, wherein such systems are configured, through automated visual inspection, to detect defects on exterior surfaces of containers. These systems include multiple cameras that are positioned to capture images of an exterior surface of a container when the conveyor passes through an inspection region. The images captured by the cameras are then analyzed to determine whether the exterior surface of the container includes a defect. These automated systems, however, can suffer from inaccuracies, as external surfaces of many types of containers (e.g., cylindrical cans) have mirror-like qualities. Therefore, light that illuminates the exterior surfaces of a container may reflect off of numerous surfaces (including surfaces of adjacent containers on the conveyor), which causes reflections of portions of the adjacent containers to appear in images of the exterior surfaces of the container under inspection. These reflections render it difficult for an automated inspection system to distinguish between: 1) a reflection in an otherwise defect-free container; and 2) a container that includes a defect.

SUMMARY

The following is a brief summary of subject matter that is described in greater detail herein. This summary is not intended to be limiting as to the scope of the claims.

Described herein is a container inspection system that is configured to ascertain whether a container being transported on a conveyor includes a defect on an exterior surface thereof. The container inspection system can detect various defects on exterior surfaces of containers, including physical defects, such as dents, creases, etc. Additionally, the container inspection system can detect defects that may occur in a design or label on an exterior surface of a container, such as an improper color being printed on the container (e.g., a color shade is incorrect), smearing, and so forth, such that the design or label does not appear as desired. The container inspection system includes a light source that is configured to emit light. In an example, the light source can be a light emitting diode (LED) or other suitable source of light. The container inspection system further includes a light director element that is configured to receive the light emitted from the light source and illuminate an exterior surface of a sidewall of a container (while the container is being transported by a conveyor) when the container enters an inspection region. In an exemplary embodiment, the light director element can direct the light emitted from the light source to create a tapering field of illumination which is incident upon the exterior surface of a sidewall of the container at relatively steep angles. More specifically, the tapering field of illumination may be conical, such that the exterior surface of a sidewall of a cylindrical container is uniformly illuminated. The steep angle of the tapering light field facilitates prevention of light from reflecting off of several surfaces in and proximate to the inspection region, thereby preventing images of adjacent containers from appearing in the exterior surface of the sidewall of the container under inspection.

The container inspection system further includes several cameras that are configured to simultaneously generate images of the exterior surface of the sidewall of the container while such surface is being illuminated by the tapering field of illumination. More specifically, the light source is strobed, such that the aforementioned container surface is illuminated for a relatively short amount of time (e.g., on the order of tens of microseconds). The cameras capture respective images of the exterior surface of the sidewall of the container while such surface is being illuminated.

In an exemplary embodiment, the cameras can be tilted relative to the sidewall of the container, such that a line of sight of a camera forms an acute angle with the exterior surface of the sidewall of the container. In other words, rather than the line of sight of the camera being orthogonal to the sidewall of the container, the camera is tilted relative to the sidewall of the container with the line of sight of the camera intersecting the sidewall of the container at approximately the center of the sidewall along its length.

The container inspection system also includes a computing system that is in communication with the cameras, wherein the computing system is configured to, for each container passing through the inspection region: 1) receive images generated by the cameras; and 2) output an indication as to whether or not the container is defective based upon the images. In an example, the container may be cylindrical and the computing system can receive images of different sides of the cylindrical container from the cameras. The computing system can unwrap the cylinder as captured in images and compare the unwrapped cylinder with a known "gold standard" (e.g., an unwrapped cylinder with no defects). The computing system may then ascertain whether or not the container includes a defect based upon such comparison.

In an exemplary embodiment, the light director element may be an ellipsoidal reflector with first and second focal points, wherein the light source is an isotropic light emitter that is positioned at the first focal point. The container, when illuminated by the tapering field of illumination, is between the first focal point and the second focal point of the ellipsoidal reflector. Further, a center axis of the container intersects the first focal point and the second focal point when the container is illuminated. In another exemplary embodiment, the light director element may be a lens, such as a Fresnel lens. In such an embodiment, the lens is positioned between the light source and the container that is being illuminated, wherein the light source is displaced from the lens by a distance that is approximately equivalent to a focal length of the lens. Further, when the container is illuminated, the optical axis of the lens is aligned with the center axis of the container under inspection. Furthermore, in such an embodiment, the light source may be a ring of light emitters, such as LED emitters. In operation, light emitted from the ring of emitters is received at the lens and the lens directs the received light to form the tapering field of illumination that substantially uniformly illuminates the exterior surface of the sidewall of the container.

In yet another exemplary embodiment, a lens of each camera can be angularly offset from its respective image sensor. Specifically, when the camera is tilted relative to the sidewall of the container, the imaging plane of the image sensor and the exterior surface of the sidewall will be angularly offset from one another, which may cause peripheries of the exterior surface of the sidewall to be out of focus in an image generated by the camera. Angularly offsetting the lens from the image sensor can at least partially correct this issue.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
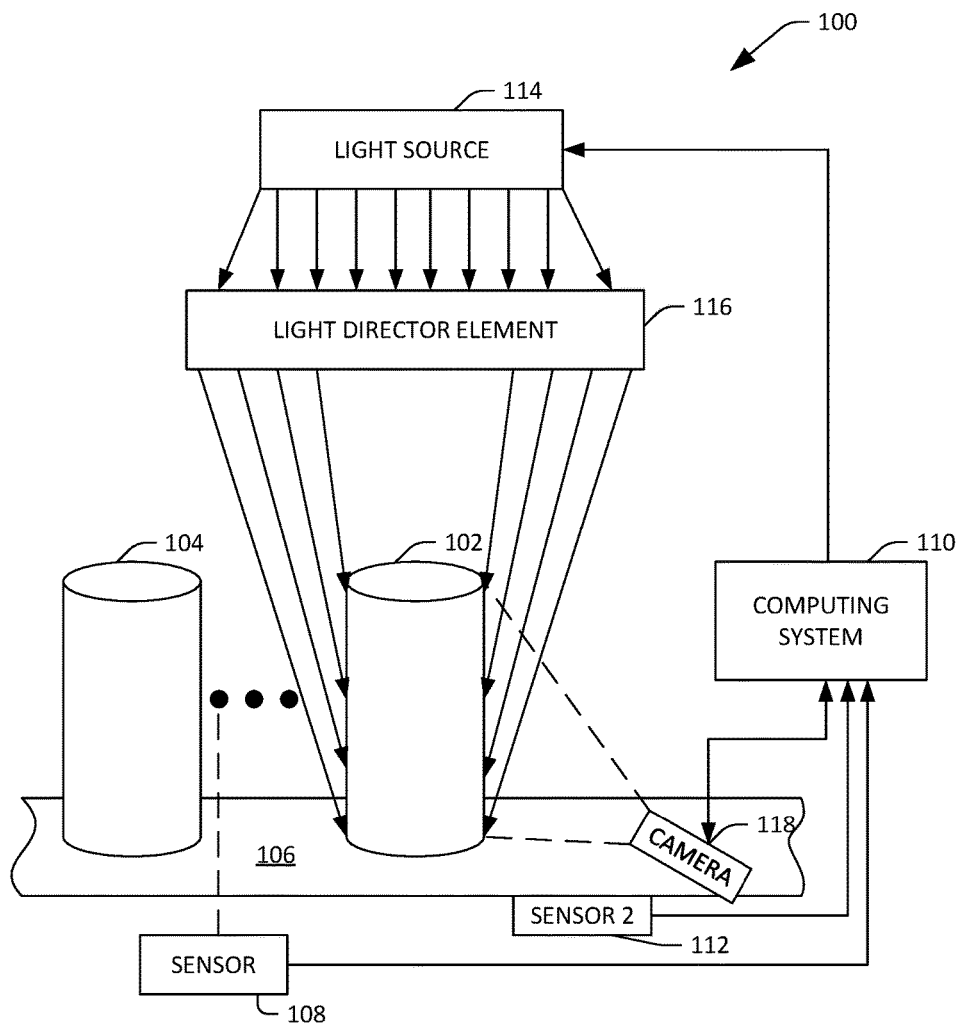
FIG. 1 is a schematic of an exemplary container inspection system.

Various technologies pertaining to a container inspection system are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Further, as used herein, the term "exemplary" is intended to mean serving as an illustration or example of something, and is not intended to indicate a preference.

With reference now to FIG. 1, an exemplary container inspection system 100 is illustrated. Generally, the container inspection system 100 is configured to inspect exterior surfaces of sidewalls of containers 102-104 for defects as the containers 102-104 are transported by a conveyor 106 through an inspection region of the container inspection system 100. In an example, the container inspection system 100 can be configured to detect functional defects in one or more of the containers 102-104, such as dents, creases, malformations in shape of one or more of the containers 102-104, etc. Further, the container inspection system 100 can be configured to detect defects in text and/or graphics printed on the exterior surfaces of the sidewalls of the containers 102-104. For instance, the container inspection system 100 can be configured to detect that the container 102 has a design printed thereon that includes an improper color (or an insufficient amount of a color). In another example, the container inspection system 100 can be configured to detect that text on a label applied to the exterior surface of the sidewall of the container 102 is smudged.

Once the container inspection system 100 identifies that a container has a defect on the exterior surface of the sidewall thereof, the container inspection system 100 can cause the defective container to be removed from the conveyor 106, such that it is not populated with a product (e.g., beverage), and therefore does not reach the hands of an end consumer. Further, the container inspection system 100 can be configured to analyze containers at a relatively high rate of speed, such as on the order of 1,000 containers per minute to 6,000 containers per minute. Moreover, the container inspection system 100 can be configured to detect defects in containers of various shapes and/or sizes. Thus, while the containers 102-104 are shown as being cylindrical, the container inspection system 100 is not limited to detecting defects in cylindrical containers. Rather, the container inspection system can be configured to detect defects in elongated cubic containers, elongated ellipsoidal containers, conical containers, etc.

The container inspection system 100 optionally includes a sensor 108 that is configured to output a signal that indicates that a container has reached a particular position relative to an inspection region of the container inspection system 100. For instance, the first sensor 108 may be an optical sensor that receives an optical beam from an optical transmitter. When a container transported by the conveyor 106 breaks the optical beam, the sensor 108 can output a signal that indicates that the optical beam has been interrupted, and thus has reached the certain position.

The container inspection system 100 further includes a computing system 110 that is in communication with the first sensor 108 and receives the signal output by the first sensor 108. The container inspection system 100 can further optionally include a second sensor 112 that is configured to monitor movement of the conveyor 106. For example, the second sensor 112 can be a rotary encoder coupled to a pulley that is attached to the conveyor 106, wherein the second sensor 112 outputs signals based upon rotation of the pulley. The computing system 110 is in communication with the second sensor 112, and receives signals output by the second sensor 112. The computing system 110, then, can ascertain position of a container relative to the first sensor 108 (and thus relative to the inspection region of the system 100) based upon signals output by the sensors 108 and 112.

The container inspection system 100 also includes a light source 114 that is in communication with the computing system 110, wherein the computing system 110 controls operation of the light source 114 based upon signals output by the sensors 108 and 112. More specifically, the computing system 110 causes the light source 114 to flash when a container is at a certain position relative to the light source 114 (such that the light source 114 strobes as the conveyor 106 transports containers). As will be described in greater detail below, the light source 114 can be a light emitting diode, a plurality of light emitting diodes arranged in a ring, a matrix of light emitting diodes, etc.

The container inspection system 100 also includes a light director element 116 that is positioned relative to the light source 114 such that light emitted by the light source 114 is received by the light director element 116. In non-limiting examples, the light director element 116 may be an ellipsoidal reflector, a lens (such as a Fresnel lens), or other suitable optical elements that are capable of directing light as described below. The light director element 116 directs the light received from the light source 114, such that a tapering field of illumination is formed, wherein the tapering field of illumination illuminates (substantially uniformly) an entirety of the exterior surface of the sidewall of the container 102 (as depicted by the arrows exiting the light director element 116).

As shown in FIG. 1, the container 102, when illuminated, is being transported by the conveyor 106 such that the container 102 is positioned between the light director element 116 and the conveyor 106. It can be ascertained that the light exiting the light director element 116 is incident upon the exterior surface of the sidewall of the container 102 at relatively steep (acute) angles. Restricting light to such illuminating field facilitates prevention of light from impacting other entities proximate the container 102 (e.g., an adjacent container on the conveyor 106), thereby preventing images of such entities from being visible on the (mirror-like) exterior surface of the sidewall of the container 102 that is subject to inspection.

The container inspection system 100 further includes a camera 118 that is in communication with the computing system 110 and is controlled by the computing system 110. More particularly, the computing system 110 causes the camera 118 to capture an image of the exterior surface of the sidewall of the container 102 while the exterior surface is being illuminated by way of the light source 114 and the light director element 116. In other words, the camera 118 generates an image of the exterior surface of the sidewall of the container 102 when such surface is illuminated. The camera 118 then provides the image to the computing system 110, and the computing system 110 generates an indication as to whether or not the container 102 is defective based upon the image generated by the camera 118. While the container inspection system 100 is illustrated as including a single camera, it is to be understood that, in operation, the container inspection system 100 can include multiple cameras 118 positioned around the container 102 when the container is in the inspection region (e.g., when the exterior sidewall of the container is illuminated by the light emitted from the light source 114). For instance, the container inspection system 100 can include three cameras, four cameras, or more, such that the cameras generate images encompassing an entirety of an exterior surface of the sidewall of the container 102.

The computing system 110 receives the images of the container 102 generated by the plurality of cameras and, in an example where the container 102 is cylindrical, unwraps the cylinder using image processing techniques. The computing system 110 may then compare the unwrapped cylinder (as captured in the images) with a "gold standard" unwrapped cylinder corresponding to a container known to be free of defects. If there is sufficient similarity between the unwrapped cylinder being inspected and the gold standard, then the computing system 110 can output an indication that the container 102 is free of defects. Conversely, if the computing system 110 compares the unwrapped cylinder with the gold standard and identifies a sufficient dissimilarity therebetween, the computing system 110 can output an indication that the container 102 is defective. The container 102 can then be removed from the conveyor 106.

As shown, in an exemplary embodiment, the camera 118 can be tilted with respect to the exterior surface of the sidewall of the container 102 under inspection. In other words, a line of sight of the camera 118 is not orthogonal to the sidewall of the container 102; rather, an angular offset exists between the line of sight of the camera and the sidewall of the container 102. The camera 118 is further positioned such that the exterior surface of the sidewall of the container 102, along its length, encompasses approximately an entirety of the vertical field of view of the camera 118. The camera 118 can be position in the manner shown for at least two reasons: 1) as the exterior surface of the sidewall of the container takes up an entirety of at least the vertical field of view of a camera 118, use of the pixels of an image sensor of the camera 118; is optimized; and 2) the tilting of the camera 118 (such that the camera is looking upwards at the container 102) allows for the camera 118 to generate an image of the sidewall of the container 102 while avoiding capturing a reflection of the conveyor 106 in the lower portion of the exterior surface of the sidewall. In other words, if the camera 118 were positioned such that the line of sight of the camera 118 were orthogonal to the sidewall the container 102 and directed towards a center of the sidewall of the container 102 along its length, a resultant image generated by the camera 118 may include a reflection of the conveyor 106 in a bottom portion of the container 102. By tilting the camera 118 in the manner shown, where the lower boundary in the vertical field of view of the camera is approximately orthogonal to the sidewall of the container 102, reflection of the conveyor 106 in the lower portion of the exterior surface of the sidewall of the container 102 is avoided. This, in turn, results in an image with less noise, resulting in improved accuracy of the container inspection system 100 relative to conventional systems.

Figure 2:
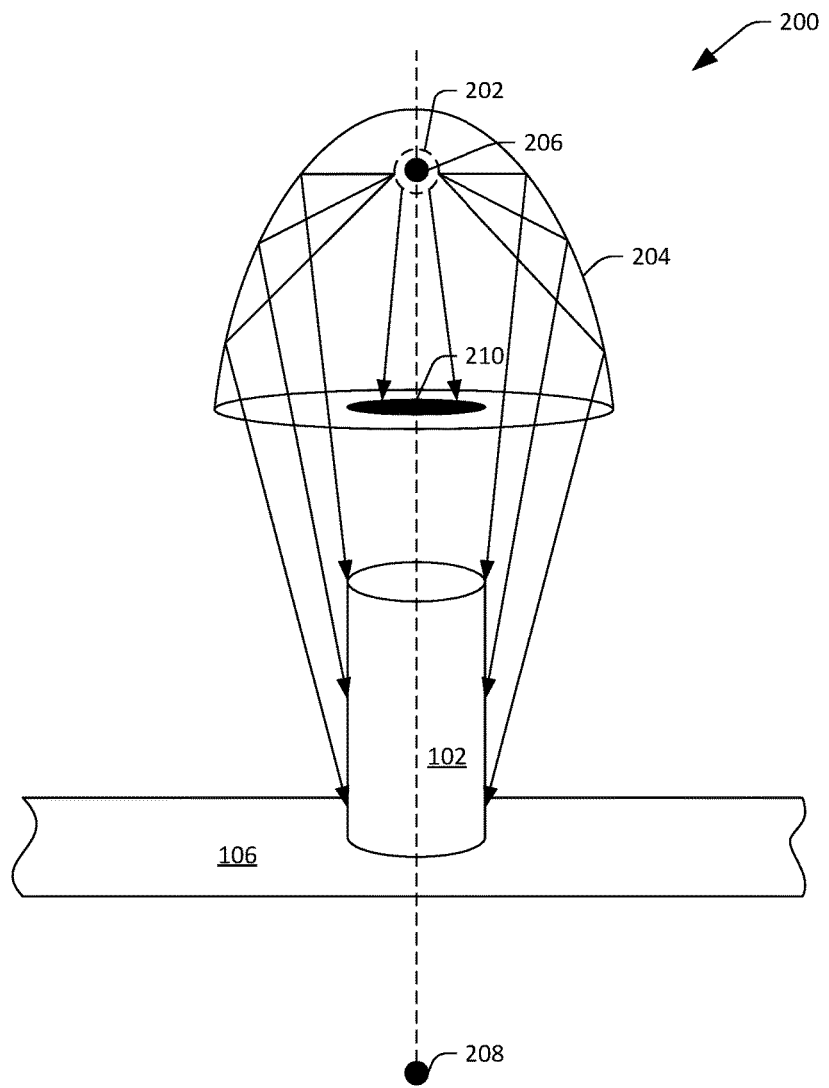
FIG. 2 is a schematic of an exemplary illumination system that is optionally included in a container inspection system.

Turning now to FIG. 2, an exemplary illumination system 200 that can be included in the container inspection system 100 is illustrated. In the illumination system 200, the light source 114 can be a light source 202 that isotropically emits light. For instance, the light source 202 can be an LED, an array of LEDs, a matrix of LEDs, or other suitable light source. The light director element 116 can be an ellipsoidal reflector 204, wherein the ellipsoidal reflector 204 includes a first focal point 206 and a second focal point 208, and wherein the container 102 under inspection is positioned between the first focal point 206 and the second focal point 208 of the ellipsoidal reflector 204. The illumination system 200 may further include a mask 210 that blocks light emitted by the light source 202 that would otherwise enter the inspection region. The blocking of such light is desirable, as light that is not illuminating the exterior surface of the sidewall of the container 102 may reflect about the inspection region, resulting in unwanted noise (e.g., reflections of a portion of an adjacent container on the conveyor 106) in images of the exterior surface of the sidewall of the container 102 generated by cameras positioned around the container 102.

As the light source 202 is positioned at the first focal point 206 of the ellipsoidal reflector 204, all light emitted by the light source 202 that reflects from the interior reflective surface of the ellipsoidal reflector will be directed towards the second focal point 208. Thus, the ellipsoidal reflector 204 can be sized and positioned relative to the conveyor 106 to account for a size of the container 102 (height and diameter) that is to be inspected. In other words, the ellipsoidal reflector 204 can be sized and positioned relative to the conveyor 106 such that light exiting the ellipsoidal reflector 204 is incident upon the exterior surface of the sidewall of the container 102 at desired (steep) angles. Further, when the computing system 110 causes the light source 202 to flash to illuminate the exterior surface of the sidewall the container 102 (and the computing system 110 causes the camera 118 to generate an image of such surface), the focal points 206 and 208 reside on a center axis (axis of symmetry) of the container 102. This causes the exterior surface of the sidewall of the container 102 to be uniformly illuminated.

Figure 3:
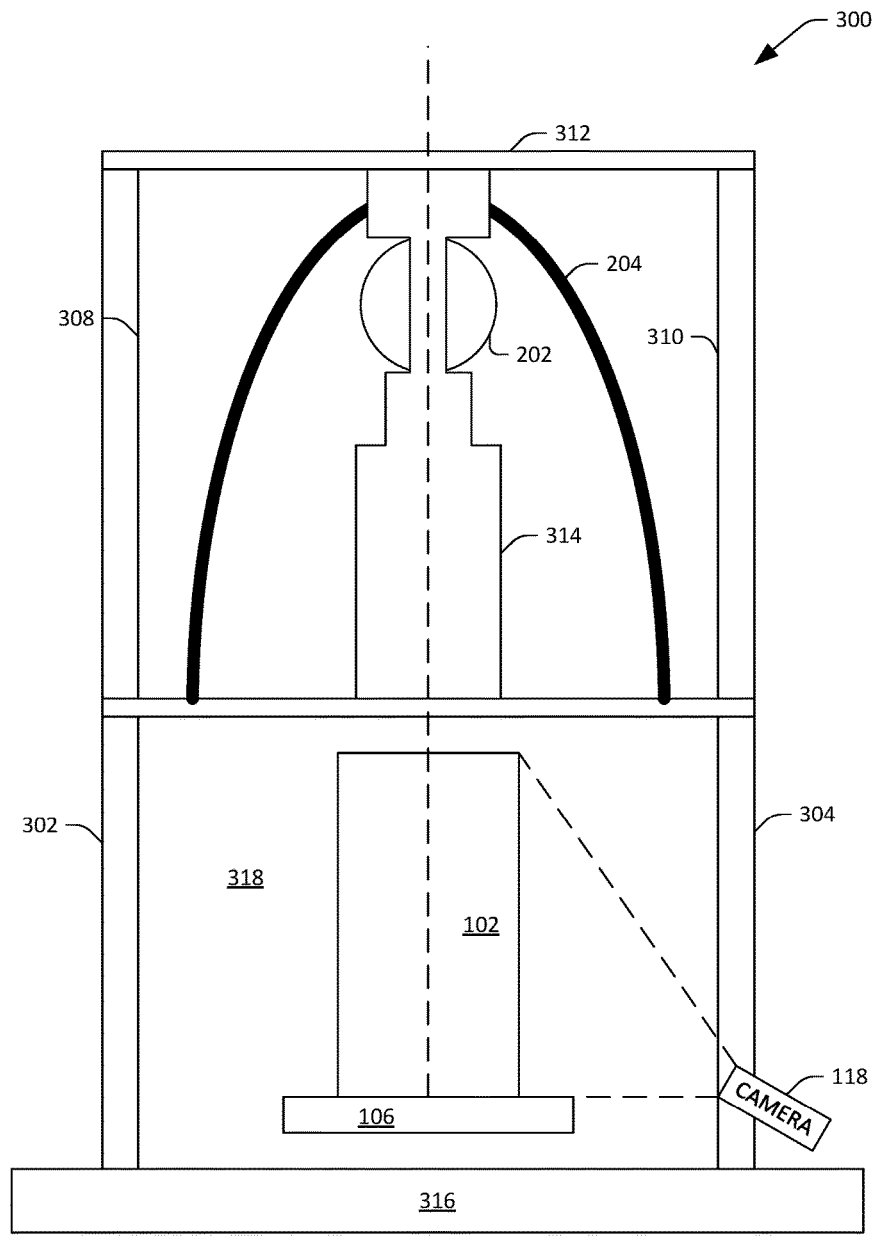
FIG. 3 is a cross-sectional view of an exemplary container inspection system.

Now referring to FIG. 3, an exemplary container inspection system 300 is illustrated. The container inspection system 300 includes supports 302 and 304, which can be posts, plates, or the like. In an exemplary embodiment, height of the supports 302 and 304 can be adjustable (to accommodate containers of varying sizes). The supports 302 and 304 support a transparent plate 306, which can be formed of plastic, glass, or the like. The container inspection system 300 also includes supports 308 and 310 that extend from the supports 302 and 304 respectively (although the supports 308 and 310 may be offset in either direction from the supports 302 and 304).

An upper support plate 312 is supported by the supports 308 and 310. Like the supports 302 and 304, height of the supports 308 and 310 can be adjustable, thereby allowing for different sizes of ellipsoidal reflectors to be supported by the supports 308 and 310. A cylindrical support post 314 extends between the upper support plate 312 and the transparent plate 306. The upper support plate 312 can be composed of some rigid material, such as steel, a hard plastic, etc. The supports 308 and 310, the upper support plate 312, and the cylindrical support post 314 support the ellipsoidal reflector 204, such that the ellipsoidal reflector 204 remains stationary relative to the supports 302 and 304. The light source 202 is supported by the cylindrical support post 314 and, as described above, is positioned approximately at the first focal point 206 of the ellipsoidal reflector 204.

The camera 118 is coupled to the support 304, and as shown in FIG. 3, the camera 118 is tilted relative to the sidewalls of containers that pass through an inspection region 318 of the container inspection system 300 (e.g., in the Z direction). With more specificity, the supports 302 and 304 are positioned on a ground plane 316, such that the supports 302 and 304 are positioned on either side of the conveyor 106. The container inspection system 300 is positioned relative to the conveyor 106 such that, for an instant in time, the first and second focal points 206 and 208 of the ellipsoidal reflector 204 will reside on center axes of containers transported through the inspection region 318 by the conveyor 106.

The cylindrical support post 314 serves several functions. First, the cylindrical support post 314 supports the ellipsoidal reflector 204, such that it remains stationary while containers are transported by the conveyor 106 through the inspection region 318. Second, the cylindrical support post 314 prevents the transparent plate 306 from sagging near its center, thereby preventing unwanted refraction. Third, the cylindrical support post 314 acts as a mask, preventing light emitted by the light emitting light source 202 from exiting the ellipsoidal reflector 204 without first reflecting off of the interior reflective surface of the ellipsoidal reflector 204. In other words, the cylindrical support post 314 prevents unwanted light from entering the inspection region 318, thus producing the tapering field of illumination referenced above.

The computing system 110 determines when the light source 202 is to be flashed and when the camera 118 is to capture an image. More specifically, the computing system 110 causes the light source to flash and the camera 118 to generate an image when a center axis of the container 102 intersects the focal points 206 and 208 of the ellipsoidal reflector 204. At least some of this light emitted by the light source 202 is reflected by the reflective surface of the ellipsoidal reflector 204, such that the light illuminates the exterior surface of the sidewall of the container 102 when the center axis of the container 102 is intersects the focal points 206 and 208 of the ellipsoidal reflector 204. The computing system 110 causes the camera 118 to capture an image of the exterior surface of the sidewall of the container 102 while such surface is illuminated. The light source 202 is flashed (rather than continuously emitting light) to minimize an amount of light entering the inspection region 318 that may otherwise reflect off of the container 102 or other containers being transported by the conveyor 106. The computing system 110 then determines whether or not the container 102 is defective, and repeats the process for each container being transported by the conveyor 106 through the inspection region 318.

Figure 4:
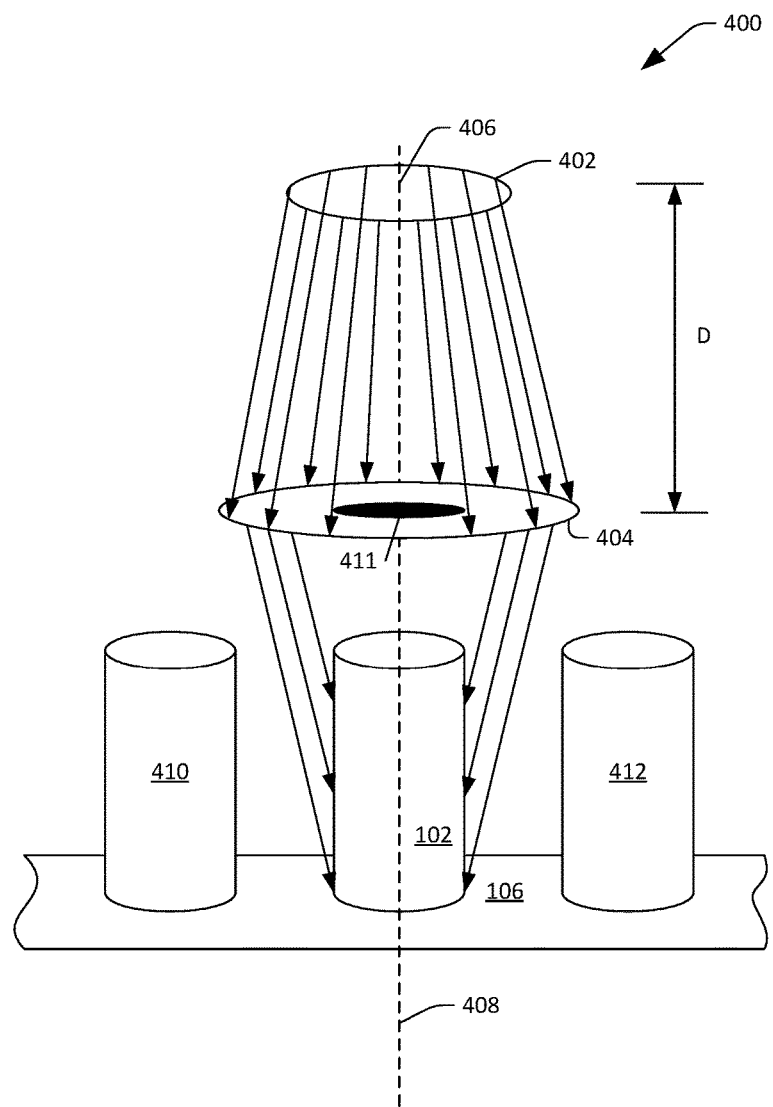
FIG. 4 is a schematic of an illumination system that can be included in an exemplary container inspection system.

Now referring to FIG. 4, another exemplary illumination system 400 is illustrated. The illumination system 400 includes a ring of light emitters 402. In other words, the light source 114 shown in FIG. 1 can be the ring of emitters 402, such as a ring of LEDs. The illumination system 400 additionally includes a lens 404 that receives light emitted by the ring of emitters 402 and directs at least a portion of such light to illuminate exterior surfaces of sidewalls of containers that pass beneath the lens 404. As shown in FIG.

4, the ring of emitters 402 is positioned relative to the lens 404, such that a center point 406 of the ring of emitters 402 is on the optical axis 408 of the lens 404. In an example, the lens 404 may be a Fresnel lens, although other types of lenses can be used. The ring of emitters 402 is displaced from the lens 404 by a distance D that is approximately equivalent to a focal length of the lens 404. Furthermore, a circumference of the ring of emitters 402 can be selected relative to a circumference of the lens 404, such that an upper surface of the lens 404 is substantially uniformly illuminated by light emitted by the ring of emitters 402. The illumination system 400 may further include a mask 411 that prevents unwanted light from entering an inspection region where containers are inspected. As described previously, the computing system 110 causes the ring of emitters 402 to flash for each of several containers 410, 102, and 412 as the containers 410, 102, and 412 are transported beneath the lens 404 by the conveyor 106. Therefore, in an example, when the container 102 is being examined, light exiting the lens 404 is incident upon the exterior surface of the sidewall of the container 102 at relatively steep angles.

Figure 5:
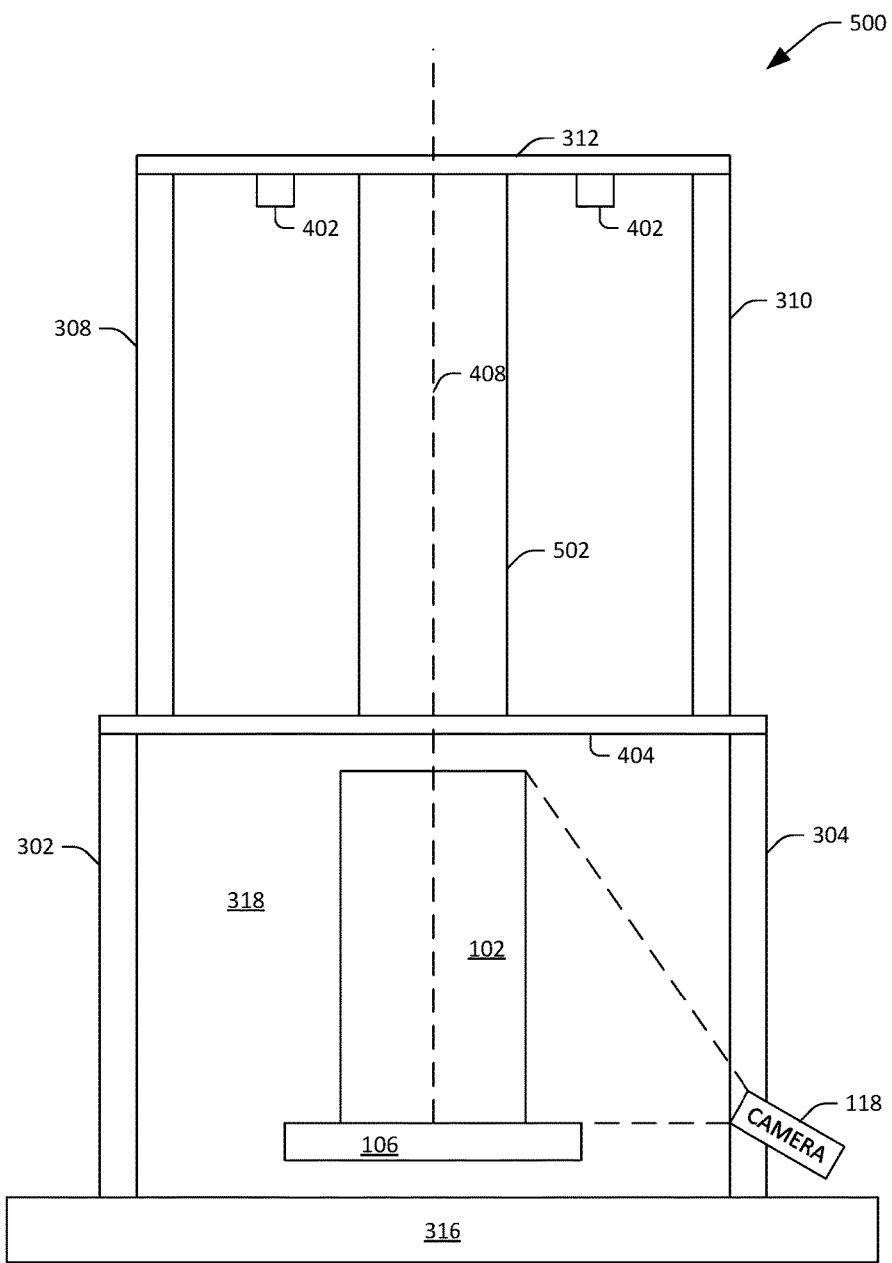
FIG. 5 is a cross-sectional view of an exemplary container inspection system.

With reference now to FIG. 5, an exemplary container inspection system 500 is illustrated. The container inspection system 500 includes the supports 302, 304, 308, 310, and 312, as described with reference to the container inspection system 300 of FIG. 3. The container inspection system 500 additionally includes the ring of emitters 402, which are supported by the upper support plate 312. The container inspection system 500 additionally includes the lens 404, which is supported by the supports 302 and 304, as well as a cylindrical support post 502 that extends between the upper support plate 312 and the lens 404. The cylindrical support post 502 is coupled to the rigid upper support plate 312, and together with the supports 302 and 304, holds the lens 404 in place relative to the conveyor 106 as containers are transported through the inspection region 318. The cylindrical support post 502 further acts as a mask, such that light exiting the lens 404 is limited to being light that illuminates the exterior surface of sidewalls of containers that pass through the inspection region 318 on the conveyor 106.

Operation of the container inspection system 500 is similar to that of the container inspection system 300. More specifically, the computing system 110 causes each emitter in the ring of emitters 402 to flash when a center axis of the container 102 (being transported on the conveyor 106 through the inspection region 318) is in alignment with the optical axis of the lens 404. At least some of the emitted light is received at the lens 404, and the lens 404 directs the light to the exterior surface of the sidewall of the container 102, thereby illuminating the exterior surface of the sidewall of the container 102. While such exterior surface is illuminated, the computing system 110 causes the camera 118 to generate an image of the exterior surface of the sidewall of the container 102, and the computing system 110 determines whether or not the container 102 is defective based upon such image.

Figure 6:
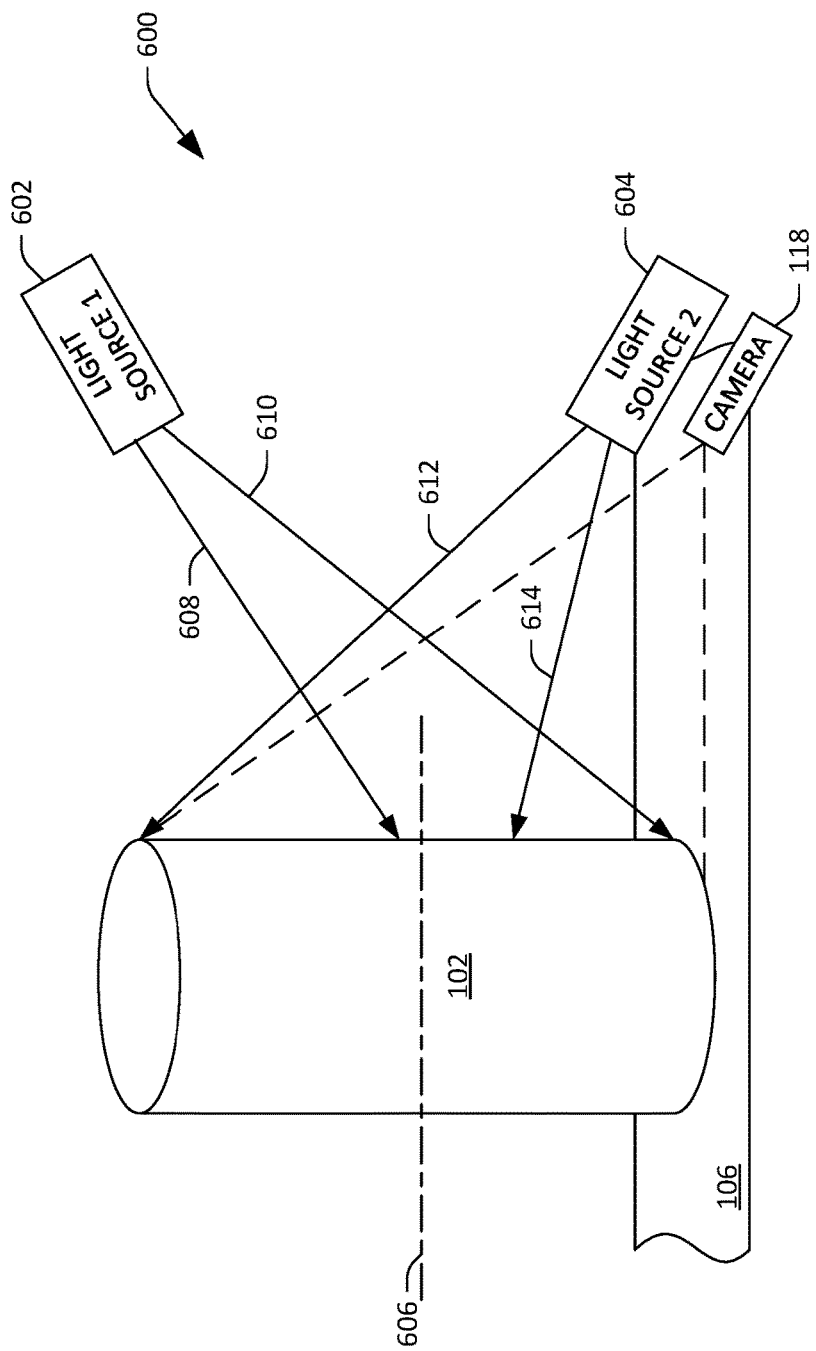
FIG. 6 is a schematic of an illumination system that can be included in an exemplary container inspection system.

With reference to FIG. 6, another exemplary container inspection system 600 is illustrated. The container inspection system 600 comprises a first light source 602 and a second light source 604, which operate in cooperation to (approximately uniformly) illuminate an exterior surface of a sidewall of the container 102. The first light source 602 is positioned above a horizontal plane 606 that bifurcates the container sidewall along its length, while the second light source 604 is positioned beneath the horizontal plane 606. The system 600 further comprises the camera 118, which is tilted relative to the exterior surface of the sidewall of the container 102.

As depicted by lines 608 and 610, the first light source 602 is configured to primarily illuminate a lower portion of the exterior sidewall of the container 102. As depicted by lines 612 and 614, the second light source 604 is configured to primarily illuminate an upper portion of the exterior surface of the sidewall of the container 102. A portion of light emitted from the first light source 602 overlaps a portion of light emitted from the second light source 604 (e.g., proximate a center portion of the container 102 where the horizontal plane 606 bifurcates the sidewall of the container). The light sources 602 and 604 are controlled by the computing system 110, such that the exterior of the sidewall of the container 102 is illuminated when the container 102 is within an examination region of the system 600. The camera 118 generates an image of the exterior surface of the sidewall of the container 102 when such surface is illuminated. The computing system 118 then outputs an indication as to whether or not the container 102 is defective based upon the image.

While the system 600 is shown as including two light sources, it is to be understood that the system 600 can include four, six, eight, or more light sources, such that an entirety of the exterior surface of the sidewall of the container 102 is illuminated by light emitted from the light sources. Further, the system 600 can include several cameras, as noted above.

Figures 7, 8:
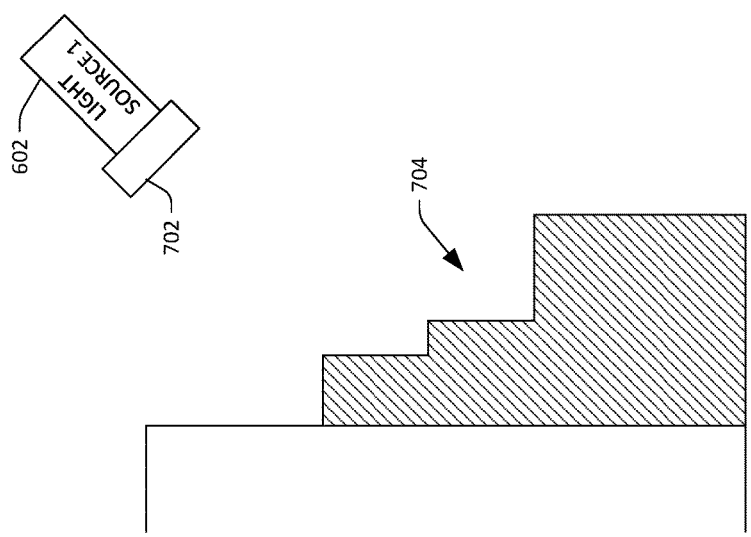
FIG. 7 is a schematic that illustrates intensity of light distributed over an exterior surface of a container sidewall, where a light source is configured to illuminate a lower portion of the exterior surface of the container sidewall.
FIG. 8 is a schematic that illustrates intensity of light distributed over an exterior surface of a container sidewall, where a light source is configured to illuminate an upper portion of the exterior surface of the container sidewall.

Turning to FIG. 7, a schematic that illustrates illumination of the lower portion of the exterior surface of the sidewall of the container 102 is depicted. The first light source 602 has a light director element 702 associated therewith that causes intensity of light that is incident upon the exterior surface of the sidewall of the container 102 to differ along a length of the sidewall (e.g., where the intensity is largest at the bottom of the exterior surface of the container 102). For instance, the light director element 702 can be an aperture or collection of apertures that causes the intensity to have a "stair-step" profile 704 along the vertical length of the sidewall of the container 102.

With reference now to FIG. 8, a schematic that illustrates illumination of the upper portion of the exterior surface of the sidewall of the container 102 is depicted. The second light source 604 has a light director element 802 associated therewith that causes intensity of light that is incident upon the exterior surface of the sidewall of the container 102 to different along a length of the sidewall (e.g., where the intensity is largest at the top of the exterior surface of the container 102). For instance, the light director element 802 can be an aperture or collection of apertures that causes the intensity to have a "stair-step" profile 804 along the vertical length of the sidewall of the container 102. As can be ascertained, when the profiles 704 and 804 are combined, the intensity profile along the exterior surface of the sidewall of the container 102 is approximately constant, such that the exterior surface of the sidewall of the container 102 is (approximately) uniformly illuminated.

Figure 9:
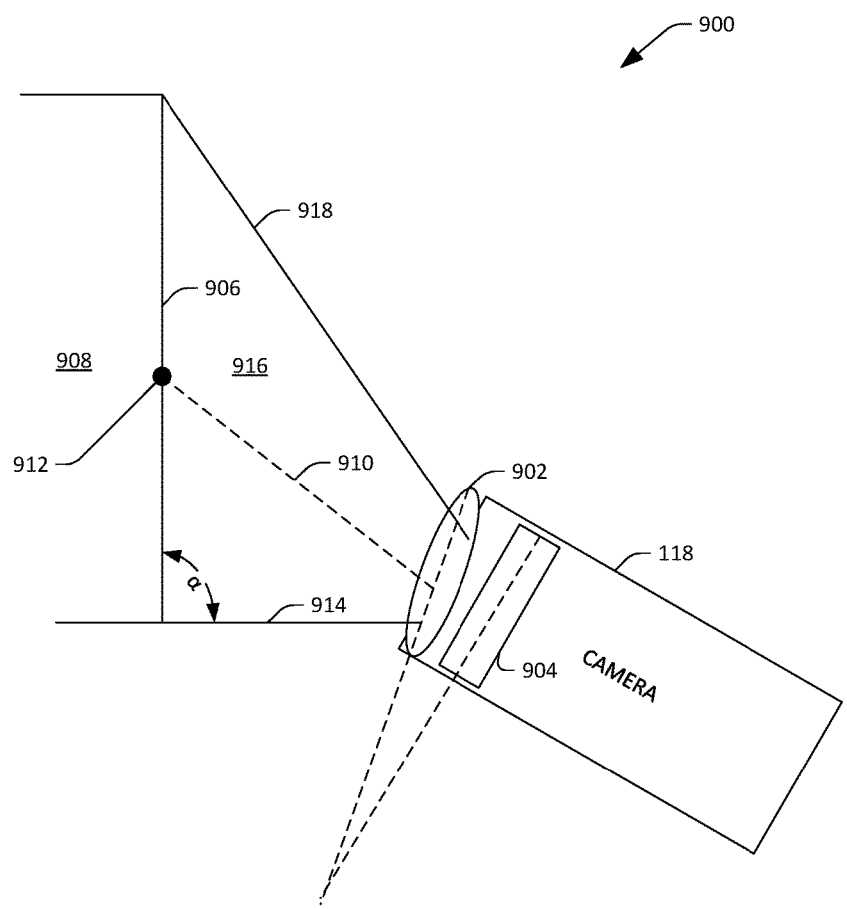
FIG. 9 is a schematic of a camera that is usable in a container inspection system.

Now referring to FIG. 9, an exemplary depiction of the camera 118 is illustrated. The camera 118 comprises a lens 902 and an image sensor 904. Generally, light entering the lens 902 is directed towards the image sensor 904, and the camera 118 generates an image based upon the light received at the image sensor 904. As described previously, the camera 118 is tilted relative to an exterior surface 906 of a sidewall of a container 908 that is subject to inspection. The camera 118 is tilted such that a line of sight 910 of the camera (i.e., a center of a field of view of the camera 118) is directed at a center point 912 of the exterior surface 906 along its length. Further, the camera 118 is tilted such that a lower boundary 914 of a vertical field of view 916 forms an angle α with respect to the exterior surface 906 that is at least 90°. This tilting prevents the camera from imaging reflections of the conveyor in the bottom portion of the container 908. Ideally, the upper boundary 918 of the vertical field of view 916 of the camera 118 intersects the upper corner of the container 908, such that the exterior surface 906 of the container 908, when under inspection, takes up an entirety of the vertical field of view of the camera 118.

When the camera 118 is tilted in this manner (and without correction), it can be ascertained that the region of the exterior surface 906 of the container 908 proximate to the center point 912 will be in focus in a resultant image, while upper and lower portions of the exterior surface 906 will be out of focus in the resultant image. To place the entirety of the exterior surface 906 in focus, the lens 902 can be angularly offset from the image sensor 904 by some suitable angle. More specifically, the lens 902 can be displaced from the image sensor 904 at a distance that is equivalent to the focal length of the lens 902. The lens 902 can be angularly offset from the image sensor 904 by some angle that is dependent upon the amount of tilt of the camera 118 relative to the exterior surface 906 of the container 908 subject to inspection. As noted previously, the container inspection system 100 may include multiple cameras, and each camera that surrounds the inspection region 318 can be tilted as shown in FIG. 9. The angular offset of the lens relative to the image sensor can be based upon the Scheimpflug principle.

Figure 10:
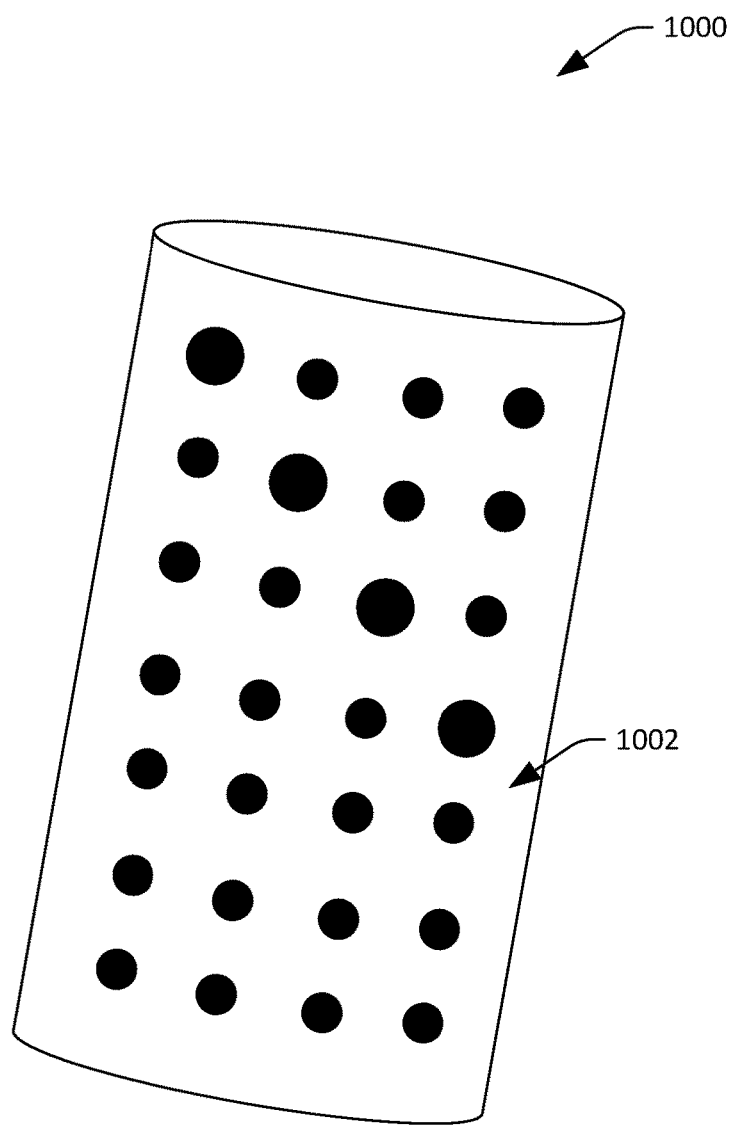
FIG. 10 is an exemplary calibration cylinder that is usable to calibrate cameras in a container inspection system.

Now referring to FIG. 10, an exemplary calibration cylinder 1000 that can be used to calibrate cameras of the container inspection system 100 is illustrated. The calibration cylinder 1000 can be sized in accordance with a size of containers that are to be inspected by the container inspection system 100. A surface of the calibration cylinder 1000 includes arrays of dots of a first color (e.g., black), arranged in rows and columns about the calibration cylinder 1000 (where the dots are referenced collectively by reference numeral 1002), wherein a background of the calibration cylinder 1000 can be of a second color (e.g., white). A number of the dots 1002 and displacement between dots can depend upon how fine the calibration needs to be. Further, each row of dots includes a plurality of dots of the same size and a single dot that is of a different size. Similarly, each column of dots includes a plurality of dots of the same size and a single dot that is of a different size. In the calibration cylinder shown in FIG. 10, the plurality of dots of the same size are larger than the plurality of dots of different sizes, although this arrangement can be reversed. Further, rather than a row (or column) having a single dot of a different size from other dots, in another example a row (or column) can have a single dot that is of a different color or shape from other dots in the row (or column).

With more specificity related to calibration, each camera in the container inspection system 100 will have its own coordinate system. It is desired to learn a mapping for all of the cameras in the container inspection system that maps each local coordinate system of each camera into a global coordinate system. With more particularity, $\hat{x}$, $\hat{y}$, and $\hat{z}$ can define a world coordinate system. An origin of the world coordinate system can be denoted as O. The container inspection system 100 may include K cameras, each considered as an ideal pinhole camera, and each with an image matrix U columns by V rows. The camera pinholes can be located in the xy plane at:

$$p_k = D \cos \Omega_k \hat{x} + D \sin \Omega_k \hat{y}, \quad (1)$$

where k=0, 1, ... K−1 is the camera index, D is the standoff distance, and $$\Omega_k = \frac{2\pi k}{K} \quad (2)$$

are the camera angles. It can be noted that the centroid of the pinholes is at O.

Each camera has its own camera coordinate system defined by the unit vectors $$\hat{u}_k = -\sin \Omega_k \hat{x} + \cos \Omega_k \hat{y}$$

$$\hat{v}_k = -\hat{z}$$

$$\hat{w}_k = -\cos \Omega_k \hat{x} - \sin \Omega_k \hat{y}, \quad (3)$$

which satisfy $$\hat{w}_k = \hat{u}_k \times \hat{v}_k$$

$$0 = \hat{u}_k \cdot \hat{v}_k = \hat{u}_k \cdot \hat{w}_k = \hat{v}_k \cdot \hat{w}_k. \quad (4)$$

The origin of the coordinate system is at the pinhole, and the optical axis is along $\hat{w}_k$. The camera is aligned so that the long sides of the image sensor are parallel to $\hat{z}$, and rows and columns of the pixel array are defined such that the rows are parallel to the short sides of the sensor (which is opposite the typical definition for cameras).

An assumption can be made regarding the physical cameras that their pinholes coincide exactly with the ideal pinholes. Other remaining non-ideal behavior of each physical camera can be compensated for by calibration-based rectification.

The following notation can be used for physical camera and ideal camera pixel coordinates, respectively: $(\bar{u}, \bar{v})$ and $(u, v)$. For notation simplicity, the subscript k may be suppressed when there is little risk of confusion.

A container coordinate system (denoted by primes) can be introduced with unit vectors $\hat{x}'$, $\hat{y}'$, and $\hat{z}'$, where the axis of the container is along $\hat{z}'$ and the origin O' coincides with the intersection of the container axis and the xy plane. The primed coordinate system is obtained from the unprimed system by rotating the unprimed system through an angle θ about the vector $\hat{z} \times \hat{z}'$ and then translating the origin of the unprimed system by T. Thus, T is the location vector of the point O' referred to in the world coordinate system.

The transformation from a point r in the world coordinate system to the same point r' in the container coordinate system is (using matrix notation and column vectors)

$$r' = \Lambda(r - T), \quad (5)$$

where $$\Lambda = \begin{pmatrix} \sin^2 \phi + \cos^2 \phi \cos \theta & -\sin \phi \cos \phi (1 - \cos \theta) & -\cos \phi \sin \theta \\ -\sin \phi \cos \phi (1 - \cos \theta) & \cos^2 \phi + \sin^2 \phi \cos \theta & -\sin \phi \sin \theta \\ \cos \phi \sin \theta & \sin \phi \sin \theta & \cos \theta \end{pmatrix} \quad (6)$$

is a rotation matrix, θ is the tilt angle of the container axis measured from $\hat{z}$, and φ is the orientation angle of the tilt measured about $\hat{z}$. The inverse transformation is:

$$r = T + \Lambda^\dagger r', \quad (7)$$

where $$\Lambda^\dagger = \begin{pmatrix} \sin^2\phi + \cos^2\phi\cos\theta & -\sin\phi\cos\phi(1-\cos\theta) & \cos\phi\sin\theta \\ -\sin\phi\cos\phi(1-\cos\theta) & \cos^2\phi + \sin^2\phi\cos\theta & \sin\phi\sin\theta \\ -\cos\phi\sin\theta & -\sin\phi\sin\theta & \cos\theta \end{pmatrix} \quad (8)$$

is the transpose of $\Lambda$, and the fact that $\Lambda'=\Lambda^\dagger$ is used for a rotation matrix.

Going forward, the primed system basis vectors can be explicitly expressed in the unprimed system as follows:

$$\hat{x}' = (\sin^2\phi + \cos^2\phi\cos\theta)\hat{x} - \sin\phi\cos\phi(1-\cos\theta)\hat{y} - \cos\phi\sin\theta\hat{z} \quad (9)$$
$$\hat{y}' = -\sin\phi\cos\phi(1-\cos\theta)\hat{x} + (\cos^2\phi + \sin^2\phi\cos\theta)\hat{y} - \sin\phi\sin\theta\hat{z}$$
$$\hat{z}' = \cos\phi\sin\theta\hat{x} + \sin\phi\sin\theta\hat{y} + \cos\theta\hat{z}$$

Details pertaining to calibration are now discussed. The calibration cylinder 1000 can have a radius $R_{cal}$ and a height $H_{cal}$ positioned with its axis along the z axis and its center at $z=Z_0$ (actually, the calibration cylinder 1000 defines $\hat{z}$ and $Z_0$). The locus of the cylinder surface of the calibration cylinder 1000 is described by:

$$s = R_{cal}\cos\omega\hat{x} + R_{cal}\sin\omega\hat{y} + \eta\hat{z}, \quad (10)$$

where the coordinates $\omega$ and $\eta$ parameterize the surface. $\omega$ can be referred to as the azimuth angle.

The surface of the calibration cylinder 1000 can include the array of dots 1002 (G columns by G rows) on a uniform white background, and the cylinder 1000 is oriented (mechanically keyed) so that the dot centers are located at $$\omega_m = \frac{2\pi m}{G} \quad (11)$$
$$\eta_n = Z_0 + \left(\frac{1}{2} - \frac{n+1}{G+1}\right)H_{cal},$$

where m, n=0, 1, ..., G−1. Dots with m=n, as noted above, can have larger diameters than the rest. The positions of the dot centers are:

$$s_{mn} = R_{cal}\cos\omega_m\hat{x} + R_{cal}\sin\omega_m\hat{y} + \eta_n\hat{z}. \quad (12)$$

The calibration cylinder 1000 can be imaged with one of the K cameras. It can be ascertained that only some subset of the dot columns are visible in this image. An automated algorithm can be used to find the centroids of the dots in the visible columns and the automated algorithm can further be used to identify which dot in each column is the large dot. Since m=n for the large dots, and since n can be determined for each large dot by counting from the top of the column, the value of m for each column can be determined. Therefore, for each camera, the computing system 110 can create a calibration table that includes the physical camera pixel coordinates $\bar{u}_{mn}, \hat{v}_{mn}$ of the dot centroids, where the values of m are restricted to the visible columns.

The goal of calibration is to allow for the transformation of the image from a physical camera into an ideal or rectified image. The rectified image is the image that an ideal pinhole camera would generate. The ideal camera has focal length f, pixel size $\delta$, and image matrix U×V. $\delta$ can be taken to be the same as the physical camera pixel size and f can be set to the specified focal length of the physical camera lens. In order to support rectified image cropping, however, it is not assumed that the rectified image matrix U×V is the same as the sensor matrix $\bar{U}\times\bar{V}$ of the physical camera.

A line drawn from the pinhole p to an imaged point s on the surface of the calibration cylinder 1000 can be considered. This line intersects the ideal camera image sensor at some point $$r = p + \lambda(s-p), \quad (13)$$

where $\lambda$ is a parameter to be determined. The vector $$r - p = \lambda(s-p) \quad (14)$$

connects the pinhole to the ideal camera image sensor, and may also be written as $$r - p = \delta(u - U_0)\hat{u} + (v - V_0)\hat{v} + f\hat{w}, \quad (15)$$

where u and v are ideal camera pixel coordinates, and $U_0$ and $V_0$ are the ideal camera pixel coordinates corresponding to the origin of the world coordinate system. Typically, $U_0 = (U-1)/2$ while $V_0$ depends on the optical configuration. Equations (14) and (15) imply $$\lambda = \frac{f}{D + s \cdot \hat{w}} \quad (16)$$
$$u = U_0 + \frac{\lambda}{\delta}s \cdot \hat{u}$$
$$v = V_0 + \frac{\lambda}{\delta}s \cdot \hat{v}$$

where the identities $p\cdot\hat{u}=p\cdot\hat{v}=0$, and $p\cdot\hat{w}=-D$ have been used.

Given the calibration cylinder parameters $R_{cal}$, $H_{cal}$, $Z_0$, and G, the positions $s_{mn}$ of all the dot centers can be calculated from (11) and (12). Given $\Omega$, D, $U_0$, $V_0$, f, and $\delta$, the ideal-camera image points ($u_{mn}$, $v_{mn}$) corresponding to the $s_{mn}$ can be calculated from (16). A rectification table can thereby be created that includes both the physical camera image points ($\bar{u}_{mn}$, $\bar{v}_{mn}$) and the ideal-camera image points ($u_{mn}$, $v_{mn}$).

The rectification table maps a relatively small number (the number of visible dots) of physical camera image points to corresponding rectified (ideal-camera) image points. In order to create a complete rectified image, data in the rectification table can be used to estimate the functions $$\bar{u} = g_u(u, v)$$
$$\bar{v} = g_v(u, v) \quad (17)$$

Then, for each pixel (u, v) in the rectified image, the corresponding (sub-pixel) location ($\bar{u}$, $\hat{v}$) in the physical camera image can be calculated from (17). The pixel value at ($\bar{u}$, $\bar{v}$) can be estimated using bilinear interpolation, and that value can be placed into the rectified image pixel.

Figure 11:
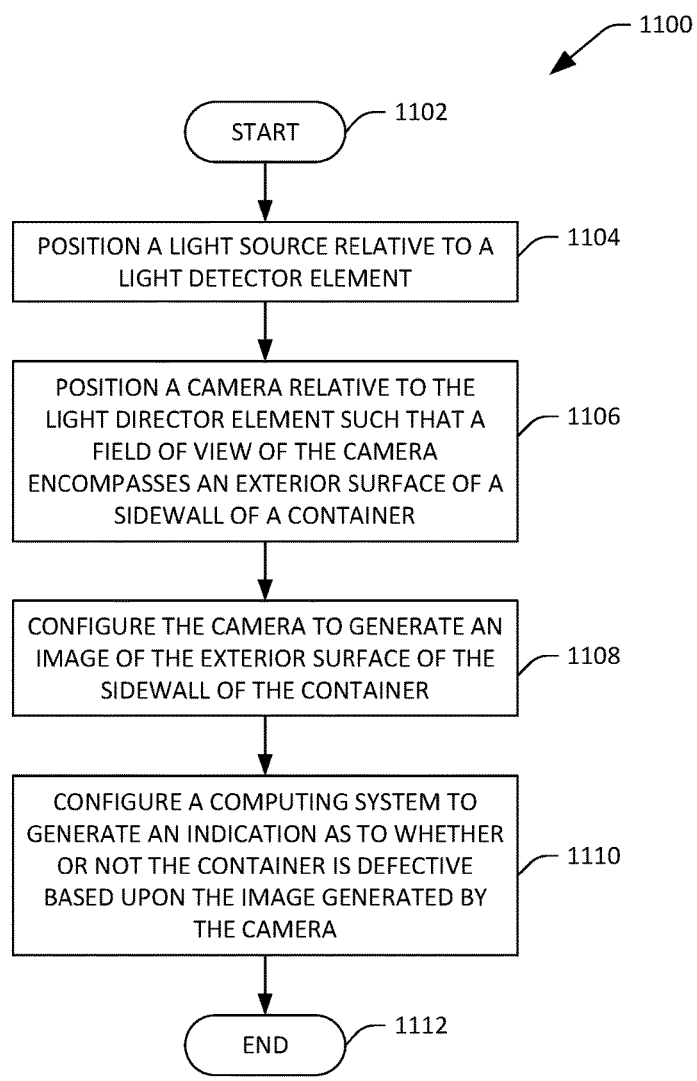
FIG. 11 is a flow diagram illustrating an exemplary methodology for configuring a container inspection system.
Figure 12:
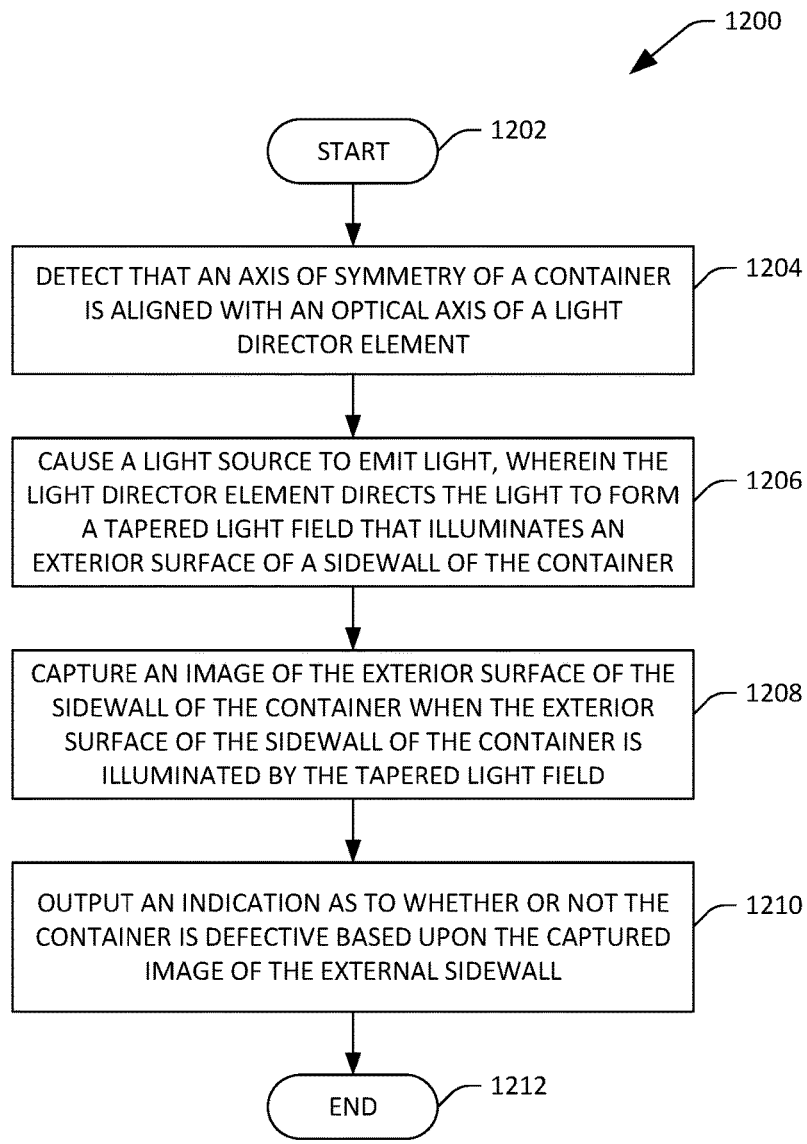
FIG. 12 is a flow diagram illustrating an exemplary methodology for operating a container inspection system.

FIGS. 11-12 illustrate exemplary methodologies relating to configuring and operating a container inspection system. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Now referring to FIG. 11, an exemplary methodology 1100 for configuring a container inspection system is illustrated. The methodology 1100 starts at 1102, and 1104 a light source is positioned relative to a light director element, such that the light emitted by the light source is received by the light director element, wherein the light director element is configured to direct the light received from the light source to generate a tapering field of light. In an example, the light source may be an ellipsoidal reflector or a Fresnel lens.

At 1106, a camera is positioned relative to the light director element, such that a field of view of the camera encompasses an exterior surface of a sidewall of a container when the external sidewall of the container is illuminated by the tapering field of light. The camera is configured to capture an image of the exterior surface of the sidewall of the container when the container is being transported by a conveyor through an inspection region of the container inspection system.

At 1108, the camera is configured to generate an image of the exterior surface of the sidewall of the container when the exterior surface of the sidewall of the container is illuminated by the tapering field of light.

At 1110, the computing system is configured to receive the image generated by the camera, and is further configured to generate an indication as to whether or not the container is defective based upon the image generated by the camera. The methodology 1100 completes at 1112.

Referring now to FIG. 12, an exemplary methodology 1200 that facilitates operating a container inspection system is illustrated. The methodology 1200 starts at 1202, and at 1204 an axis of symmetry (a center axis) of a container that is to be inspected is detected as being aligned with the optical axis of a light director element. When the light director element is an ellipsoidal reflector, the optical axis is defined by focal points of the ellipsoidal reflector. When the light director element is a lens, the optical axis of the light director element is the optical axis of the lens.

At 1206, responsive to detecting that the axis of symmetry of the container is aligned with the optical axis of the light director element, a light source is caused to emit light and the light director element directs such light to form a tapered light field that illuminates an exterior surface of a sidewall of the container. As described previously, this is performed while the container is being transported at a relatively high rate of speed along a conveyor.

At 1208, an image of the exterior surface of the sidewall of the container is captured in the short amount of time that the exterior service of the sidewall of the container is illuminated by the tapered light field. At 1210, this image is analyzed and an indication is output as to whether or not the container is defective based upon the captured image of the exterior surface of the sidewall the container. The methodology 1200 completes at 1212.

Figure 13:
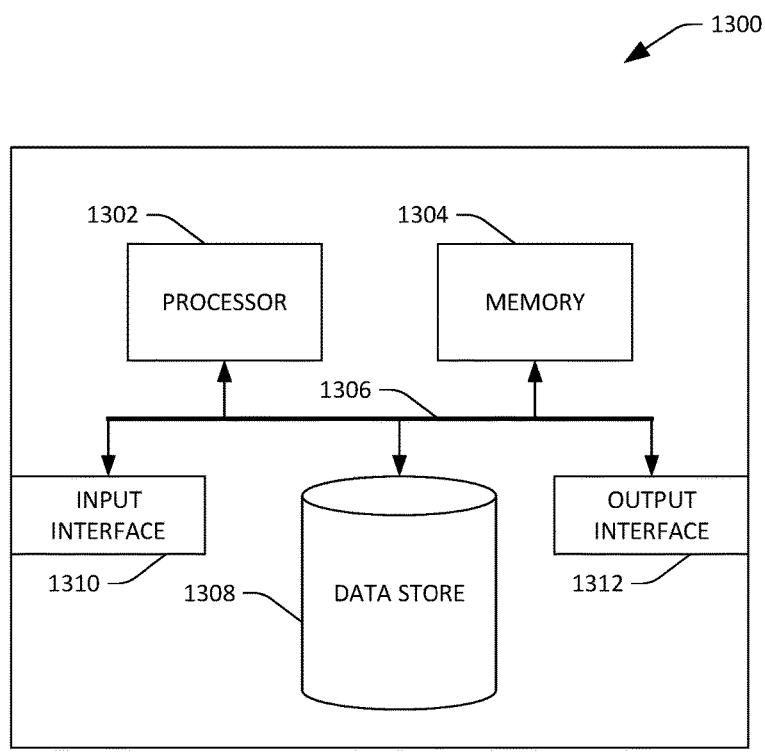
FIG. 13 is an exemplary computing device.

Referring now to FIG. 13, a high-level illustration of an exemplary computing device 1300 that can be included in the computing system 110 is illustrated. The computing device 1300 includes at least one processor 1302 that executes instructions that are stored in a memory 1304. The instructions may be, for instance, instructions for implementing functionality described as being carried out by the computing system 110, as described above. The processor 1302 may access the memory 1304 by way of a system bus 1306. In addition to storing executable instructions, the memory 1304 may also store images, threshold values, etc.

The computing device 1300 additionally includes a data store 1308 that is accessible by the processor 1302 by way of the system bus 1306. The data store 1308 may include executable instructions, images, etc. The computing device 1300 also includes an input interface 1310 that allows external devices to communicate with the computing device 1300. For instance, the input interface 1310 may be used to receive instructions from an external computer device, from a user, etc. The computing device 1300 also includes an output interface 1312 that interfaces the computing device 1300 with one or more external devices. For example, the computing device 1300 may display text, images, etc. by way of the output interface 1312.

It is contemplated that the external devices that communicate with the computing device 1300 via the input interface 1310 and the output interface 1312 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 1300 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 1300 may be a distributed system. Thus, for instance, several devices may be in communication by way of a network connection and may collectively perform tasks described as being performed by the computing device 1300.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A container inspection system comprising:
   a light source that is configured to emit light;
   a light director element that is configured to receive the light emitted from the light source and to concurrently illuminate an entirety of an exterior surface of a sidewall of a container that is being transported on a conveyor, the light director element illuminates the entirety of the exterior surface with a tapering, conical field of illumination that is incident upon the exterior surface at acute angles, wherein the container, when the exterior surface is illuminated, is positioned between the light director element and the conveyor;
   a camera that is configured to generate an image of a portion of the exterior surface of the sidewall of the container when the entirety of the exterior surface of the sidewall is concurrently illuminated by the tapering, conical field of illumination; and
   a computing system in communication with the camera, the computing system is configured to receive the image generated by the camera and output an indication as to whether or not the container is defective based upon the image.

2. The container inspection system of claim 1, the light director element being an ellipsoidal reflector, wherein the light source is positioned at a focal point of the ellipsoidal reflector, and further wherein the tapering, conical field of illumination has an apex at a second focal point of the ellipsoidal reflector.

3. The container inspection system of claim 1, the light director element being a lens having an optical axis, the light source being a ring of lights having a center point, wherein the ring of lights is parallel to the lens and the center point of the ring of lights is on the optical axis of the lens.

4. The container inspection system of claim 3, the lens being a Fresnel lens.

5. The container inspection system of claim 3, the lens having a focal length, wherein the ring of lights is displaced from the lens at a distance of the focal length of the lens.

6. The container inspection system of claim 1, further comprising a sensor that is in communication with the computing system, wherein the computing system is in communication with the light source, and further wherein the computing system is configured to cause the light source to emit the light based upon a signal output by the sensor, the signal output by the sensor indicative of a position of the container on the conveyor relative to the light source.

7. The container inspection system of claim 6, the container having a center axis, the light director element having an optical axis, and wherein the computing system is configured to cause the light source to emit the light when the center axis of the container is aligned with the optical axis of the light director element.

8. The container inspection system of claim 7, wherein the container is cylindrical.

9. The container inspection system of claim 1, wherein the camera is tilted relative to the sidewall of the container such that a line of sight of the camera is incident upon the exterior surface of the sidewall of the container at an acute angle.

10. The container inspection system of claim 9, wherein the camera comprises a lens and an image sensor, wherein the lens is angularly offset from the image sensor.

11. The container inspection system of claim 9, wherein the camera is positioned relative to the light director element such that the exterior surface of the sidewall of the container takes up an entirety of a vertical field of view of the camera when the exterior surface is illuminated with the tapering, conical field of illumination.

12. A method for configuring a container inspection system, the method comprising:
    positioning a light source relative to a light director element such that light emitted by the light source is received by the light director element, the light director element configured to direct the light received from the light source to generate a tapering, conical field of light that concurrently illuminates an entirety of an exterior surface of a sidewall of a container that is being inspected;
    positioning a camera relative to the light director element such that a field of view of the camera encompasses a portion of the exterior surface of the sidewall of the container when the entirety of the exterior surface of the sidewall is concurrently illuminated by the tapering, conical field of light, wherein the container is being transported by a conveyor when illuminated by the tapering, conical field of light;
    configuring the camera to generate an image of the exterior surface of the sidewall of the container when the exterior surface is illuminated by the tapering, conical field of light;
    configuring a computing system to:
      receive the image generated by the camera; and
      generate an indication as to whether or not the container is defective based upon the image generated by the camera.

13. The method of claim 12, wherein the light director element is an ellipsoidal reflector, and wherein positioning the light source relative to the light director element comprises placing the light source at a focal point of the ellipsoidal reflector.

14. The method of claim 13, further comprising:
    configuring the computing system to cause the light source to emit the light based upon an indication that a center axis of the container intersects with the focal point of the ellipsoidal reflector.

15. The method of claim 12, wherein the light director element is a lens, and wherein positioning the light source relative to the light director element comprises positioning the light source at a distance from the lens that is approximately equivalent to a focal length of the lens.

16. The method of claim 15, wherein the lens is a Fresnel lens.

17. The method of claim 12, wherein configuring the camera to generate the image of the exterior surface of the sidewall of the container when the exterior surface is illuminated by the tapering, conical field of light comprises:
positioning the camera such that a line of sight of the camera forms an acute angle with the exterior surface when the exterior surface is illuminated by the tapering, conical field of light.

18. The method of claim 17, wherein configuring the camera to generate the image of the exterior surface of the sidewall of the container when the exterior surface is illuminated by the tapering, conical field of light comprises:
positioning the camera such that the line of sight of the camera intersects the exterior surface of the sidewall of the container at a center of the exterior surface along its length when the exterior surface is illuminated by the tapering, conical field of light.

19. The method of claim 18, wherein configuring the camera to generate the image of the exterior surface of the sidewall of the container when the exterior surface is illuminated by the tapering, conical field of light comprises:
angularly offsetting a lens of the camera from an image sensor of the camera to correct for out of focus caused by the acute angle formed between the line of sight of the camera and the exterior surface of the sidewall of the container.

20. A container inspection system comprising:
means for emitting light when a container transported by a conveyor is detected as being at a particular position;
means for forming a tapered, conical light field with the light, wherein the means for forming the tapered, conical light field concurrently illuminates an entire exterior surface of a sidewall of the container with the tapered light when the container is detected as being at the particular position; and
means for generating an image of the exterior surface of the sidewall of the container when the container is detected as being at the particular position.

* * * * *